United States Patent
Casey, II

(10) Patent No.: US 7,993,327 B2
(45) Date of Patent: Aug. 9, 2011

(54) MULTI-SLIT HIGH FLOW VALVE

(75) Inventor: Thomas V. Casey, II, Grafton, MA (US)

(73) Assignee: Navilyst Medical, Inc., Marlborough, MA (US)

(*) Notice: Subject to any disclaimer, the term of this patent is extended or adjusted under 35 U.S.C. 154(b) by 0 days.

(21) Appl. No.: 11/834,101

(22) Filed: Aug. 6, 2007

(65) Prior Publication Data

US 2008/0097341 A1    Apr. 24, 2008

Related U.S. Application Data

(60) Provisional application No. 60/853,917, filed on Oct. 24, 2006.

(51) Int. Cl.
- A61M 25/18 (2006.01)
- A61M 25/00 (2006.01)
- A61M 5/00 (2006.01)

(52) U.S. Cl. .......................... 604/537; 604/528; 604/247

(58) Field of Classification Search ............... 604/43, 604/44, 45, 164, 168, 247, 264, 280, 281, 604/282, 164.13, 523, 528, 537
See application file for complete search history.

(56) References Cited

U.S. PATENT DOCUMENTS

| | | | | |
|---|---|---|---|---|
| 4,543,087 A * | 9/1985 | Sommercorn et al. | ......... | 604/43 |
| 4,801,297 A * | 1/1989 | Mueller | .............. | 604/523 |
| 5,147,332 A * | 9/1992 | Moorehead | ............ | 604/247 |
| 5,571,093 A * | 11/1996 | Cruz et al. | ............ | 604/270 |
| 5,807,349 A * | 9/1998 | Person et al. | ............ | 604/247 |
| 6,786,884 B1 * | 9/2004 | DeCant et al. | .......... | 604/43 |
| 7,316,655 B2 * | 1/2008 | Garibotto et al. | ........ | 600/585 |
| 2002/0156430 A1 * | 10/2002 | Haarala et al. | ........... | 604/247 |
| 2002/0165492 A1 * | 11/2002 | Davey et al. | ........... | 604/167.04 |
| 2004/0064128 A1 * | 4/2004 | Raijman et al. | .......... | 604/523 |
| 2005/0043703 A1 * | 2/2005 | Nordgren | .............. | 604/500 |
| 2005/0149116 A1 | 7/2005 | Edwards et al. | | |
| 2005/0171490 A1 | 8/2005 | Weaver et al. | | |
| 2005/0283122 A1 * | 12/2005 | Nordgren | .............. | 604/247 |

FOREIGN PATENT DOCUMENTS

| | | |
|---|---|---|
| EP | 0 864 336 | 9/1998 |
| WO | 01/74434 | 10/2001 |

* cited by examiner

Primary Examiner — Theodore J Stigell
Assistant Examiner — William Carpenter
(74) Attorney, Agent, or Firm — Bingham McCutchen LLP

(57) ABSTRACT

A valve may include (a) a housing defining a valve lumen adapted for fluid connection with a lumen of a catheter; (b) a substantially conical valve member coupled to the housing and extending across the valve lumen to control flow therethrough; (c) a plurality of slits extending through the valve member and separated from one another circumferentially around the valve member; and (d) a ramp formed within a distal end of the valve lumen extending proximally from a distal tip of the valve member toward a ramp vertex separated from the distal tip by a predetermined distance.

17 Claims, 1 Drawing Sheet

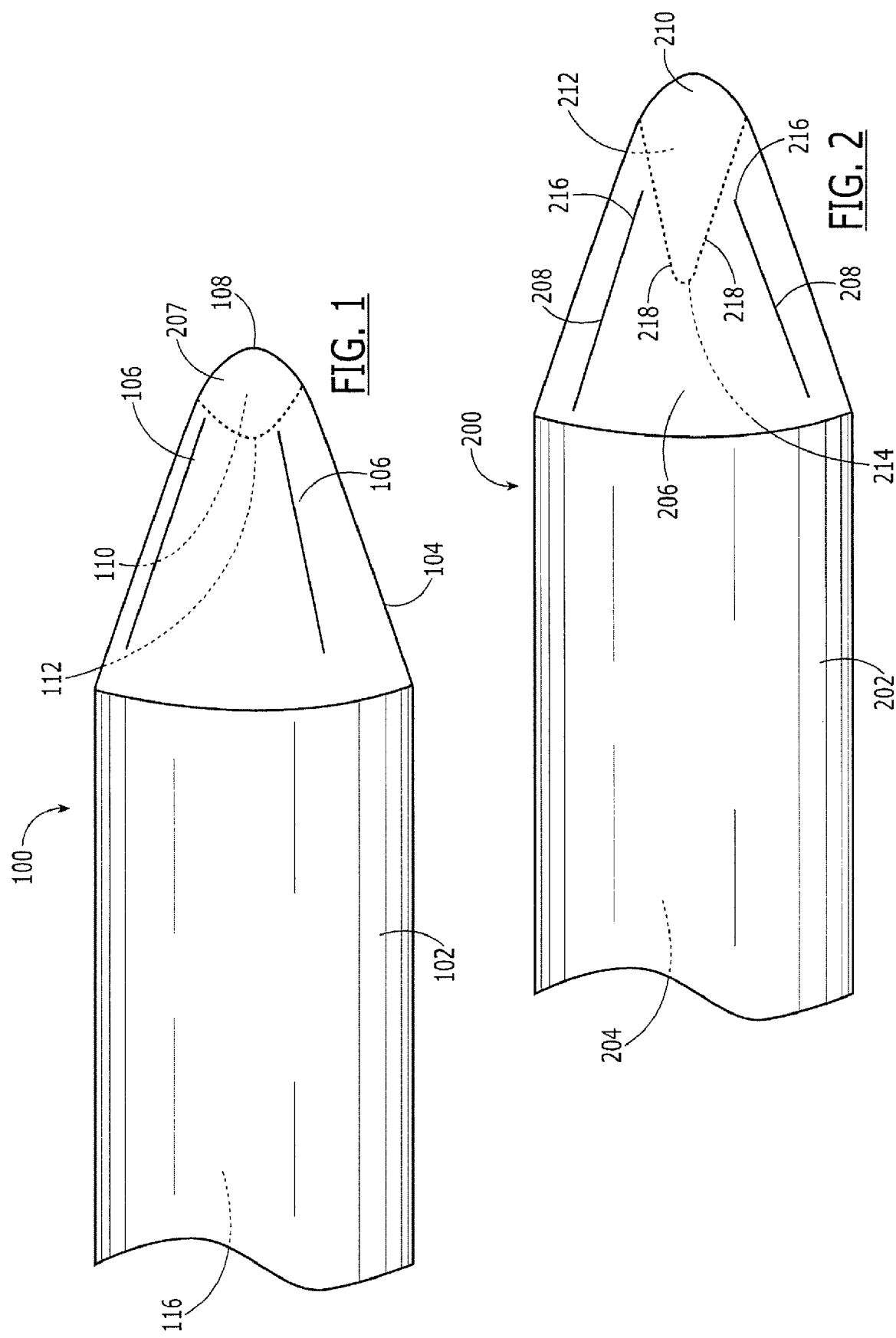

MULTI-SLIT HIGH FLOW VALVE

PRIORITY CLAIM

This application claims the priority to the U.S. Provisional Application Ser. No. 60/853,917, entitled "Multi-Slit High Flow Valve," filed Oct. 24, 2006. The specification of the above Provisional application is incorporated herewith by reference.

BACKGROUND

When repeated and prolonged access to the vascular system is required, it is often impractical and dangerous to insert and remove a needle for each session. Thus, patients are often fitted with semi-permanent catheters to facilitate vascular access and reduce discomfort.

When not in use, these semi-permanent catheters may be sealed, for example, by valves such as Pressure Actuated Safety Valves (PASV) which open only when fluid pressure exceeds a preselected threshold pressure. PASV's often include a slitted membrane with edges that separate from one another to open the valve only when fluid pressure applied thereto exceeds a threshold level and which are drawn together to seal the valve whenever the pressure falls below this threshold level.

In addition to typical fluid infusion and withdrawal procedures, certain patients require power injections of fluids to, for example, perform CT and/or MR studies. Using the same peripherally inserted central catheter (PICC) for the typical infusion/withdrawal procedures as well as the power injections simplifies these procedures. However, as power injections require considerably higher flow rates and pressures than most other procedures, using the same PICC for power injections subjects the PICC to stress levels which are not sustainable by conventional PASV's. Some recent designs of high flow membranes for PASV's have been found suitable for power injection including, for example, U.S. Published Patent Application No. 20050043703 to Greg Nordgren ("the '703 application), which is hereby incorporated by reference in its entirety. The '703 application describes conical, high flow rate, multi-slit membranes for PASV's.

SUMMARY OF THE INVENTION

In one aspect, the present invention is directed to a valve comprising a housing defining a valve lumen adapted for fluid connection with a lumen of a catheter and a substantially conical valve member coupled to the housing and extending across the valve lumen to control flow therethrough in combination with a plurality of slits extending through the valve member and separated from one another circumferentially around the valve member and a ramp formed within a distal end of the valve lumen extending proximally from a distal tip of the valve member toward a ramp vertex separated from the distal tip by a predetermined distance.

BRIEF DESCRIPTION OF DRAWINGS

FIG. 1 shows an exemplary embodiment of the multi-slit high flow valve membrane according to the invention; and FIG. 2 shows a second exemplary embodiment of the multi-slit high flow valve according to the invention.

DETAILED DESCRIPTION

The present invention may be further understood with reference to the following description and to the appended drawings, wherein like elements are referred to with the same reference numerals. The present invention relates to valves used selectively sealing a proximal end of a catheter and more specifically relates to high flow multi-slit membranes used in catheter valves.

When an internal shape of a conic valve mirrors the external shape (i.e., the internal space is conic), difficulties may arise when attempting to pass a guidewire through the catheter. The tips of guidewires or other instruments may become trapped in the concave vertex of the valve instead of passing through a slit. According to the exemplary embodiments of the present invention, the internal shape of the cone tip of the valve membrane is modified to divert and direct a guidewire or other instrument inserted therethrough into one of the slits. According to exemplary embodiments of the present invention, a valve membrane for a high flow PASV comprises a ramp feature within the conic tip to divert the instrument away from a vertex of the conic tip toward one or more of the slits.

As shown in FIG. 1, a high flow multi-slit membrane for use in a PASV valve 100 according to the invention comprises a tubular housing 102 with a generally conical valve member 104 extending from a distal end thereof. Those skilled in the art will understand that the valve member 104 may be integrally formed with the housing 102 or may be bonded thereto by welding, molding operations, etc. Furthermore, an outer surface of the valve member 104 preferably mates with a distal end of the housing 102 to form a smooth junction. In addition, those skilled in the art would understand that the housing 102 may be integrally formed with or connected to a catheter within which the valve 100 is to be deployed. Alternatively, the housing 102 and the valve member 104 may be located within a connector to be coupled to a proximal end of the catheter. The valve member 104 presents a concave face to flow impinging upon it from the lumen 110 of the tubular housing 102 with multiple slits 106 being formed in the membrane 104 to permit the passage of fluid when they are open. When the slits 106 are closed, the membrane 104 prevents passage of fluids therethrough. Typically, the membrane 104 and slits 106 are designed to open only when a fluid pressure exerted thereagainst is at least a desired threshold pressure. When the pressure is below this threshold pressure, the valve is closed. This valve 100 is bi-directional with the pressure required to aspirate fluids preferably being greater than that required for injection. For example, the pressure required to aspirate fluids from the valve 100 may be three times that required to inject fluids through the valve 100.

In the exemplary embodiment shown in FIG. 1, the slits 106 extend substantially longitudinally (i.e., in a plane including a longitudinal axis of the valve 100) along the surface of the valve member 104, and may be spaced evenly around a circumference thereof or in any desired pattern. The slits 106 generally do not extend into a vertex portion 108 of the member 104, so that the member 104 remains sealed whenever the pressure is below the threshold value. A ramp 110 is formed inside the vertex portion 108 to direct objects inserted therethrough to the one or more of the slits 106.

Thus, instead of becoming stuck at the vertex of the interior of the cone tip 108, the end of a guidewire (or other instrument) encounters a surface 112 of the ramp 110 which deflects it away from the longitudinal axis of the valve 100 toward the distal ends of the slits 106. As would be understood by those skilled in the art, the surface 112 may be formed in any shape serving to deflect an instrument inserted through the valve away from the longitudinal axis as it approaches the vertex portion 108. For example, the surface 112 may comprise a dome shaped portion with a surface that is convex away from the cone tip 108.

In addition to facilitating passage of a guidewire, valves according to the present invention improve the flow of fluid therethrough. For example, the exemplary ramp 110 eliminates a location in which blood may pool (e.g., the concavity of the vertex portion 108), thereby reducing the risk of thrombus formation. The improved design also promotes an optimal flow through the valve by eliminating a stagnation spot in the tip cone where the fluid flow stagnates.

Additional benefits of the exemplary embodiment of the valve according to the invention include increased total slit area compared to a conventional flat membrane, thus permitting the higher flow rates necessary for power injection. The exemplary valve also shows a reduced overall diameter for a given size of valve, consequently reducing the size of the housing required. In addition, as described above, the exemplary conic valve may be manufactured by molding, which is an easily repeatable and cost effective process.

As shown in FIG. 3, a valve 200 according to a second embodiment of the invention comprises a housing 202 defining a lumen 204 extending therethrough. As in the embodiment described above, a valve portion 206 of the valve 200 is generally conical in shape and, in most applications, will form the distal end of the valve 200. A concave side of the interior of the valve portion 206 faces incoming fluid in the lumen 204 with multiple slits 208 extending through the valve portion 206 to permit flow from the lumen 204 to an exterior of the valve 200. As described above in regard to the slits 106 of the valve 100, the slits 208 are open only when subject to a fluid pressure of at least a threshold level and remain closed at all other times. As in the embodiment previously described, the slits 208 extend in a substantially longitudinal direction along the surface of the valve membrane 204, converging toward a tip 210 of the cone of the valve portion 206. Those skilled in the art will understand that a valve including only a single slit may also be employed. However, the flow rates for such single slit valves will be lower than that for multi-slit valves. In addition, the slits may be curved or in any other desired shape so long as the do not open through the distal-most tip of the housing.

An elongated ramp 212 which extends inside the valve portion 206 upstream from the tip 210 may be, for example, conical with a proximal tip 214 that extends proximally beyond distal ends 216 of the slits 226. The surface 218 of the elongated ramp 212 is shaped to direct an object such as the tip of a guidewire moving distally through the lumen 204 away from the tip 210. The slope of the surface 218 (i.e., for a conical ramp 212, an angle of the cone) is preferably selected to direct a distal tip of an instrument inserted through the lumen 204 radially away from a longitudinal axis of the valve 200 toward the distal ends 216 of the slits 208 preventing the instrument from becoming trapped in the tip 210.

As an alternative to the conic shape described for the ramp 212, other shapes may be used to more positively guide the tip of an instrument into the slits 208. Those skilled in the art will understand that any shape for the ramp 212 may be used which slopes toward the slits 208 to guide the tip of an instrument thereto.

The present invention has been described with reference to specific exemplary embodiments. Those skilled in the art will understand that changes may be made in details, particularly in matters of shape, size, material and arrangement of parts. Accordingly, various modifications and changes may be made to the embodiments. The specifications and drawings are, therefore, to be regarded in an illustrative rather than a restrictive sense.

The invention claimed is:

1. A valve, comprising:
   a housing defining a valve lumen adapted for fluid connection with a lumen of a catheter;
   a substantially conical valve member coupled to the housing and extending across the valve lumen to control flow therethrough;
   a plurality of slits extending through the valve member and separated from one another circumferentially around the valve member, wherein said plurality of slits are configured to open such that they are in fluid communication with one another through the valve lumen; and
   a ramp formed within a distal end of the valve lumen extending proximally from a distal tip of the valve member toward a ramp vertex separated from the distal tip by a predetermined distance, wherein the ramp includes a surface that intersects a longitudinal axis of the valve, wherein the surface is shaped to direct an instrument inserted through the valve lumen away from the longitudinal axis of the valve as the instrument approaches the distal tip, and wherein a proximal end of the ramp is proximal of a distal end of a first one of the slits.

2. The valve of claim 1, wherein the ramp is substantially conical.

3. The valve of claim 1, wherein the ramp is shaped substantially as a portion of a sphere.

4. The valve of claim 1, wherein the valve member and ramp are molded.

5. The valve of claim 1, wherein the ramp projects into the valve lumen proximally beyond a distal end of a first one of the slits.

6. The valve of claim 1, wherein the ramp projects into the valve lumen proximally beyond distal ends of all of the slits.

7. The valve of claim 1, wherein the proximal end of the ramp is proximal of distal ends of all of the slits.

8. The valve of claim 1, wherein the slits are biased by a resilience of the material of the valve toward a closed position in which the valve is sealed and can be moved by a fluid to an open position permitting fluid flow therethrough only when the fluid pressure applied to the valve exceeds a predetermined threshold value.

9. A catheter, comprising:
   a valve mounted within a lumen of a catheter to control flow therethrough, the valve including a proximal opening having a diameter substantially equal to a diameter of the lumen and tapering gradually to a vertex at a distal end of the valve;
   a plurality of slits extending through the valve and separated from one another circumferentially around the valve, wherein said plurality of slits are configured to open such that they are in fluid communication with one another through the lumen; and
   a ramp formed on a concave side of the valve and projecting from the vertex toward the proximal opening, wherein the ramp includes a surface that intersects a longitudinal axis of the catheter, wherein the surface is shaped to direct an instrument inserted through the valve lumen away from the longitudinal axis of the valve as the instrument approaches the distal end, and wherein a proximal end of the ramp is proximal of a distal end of at least one of the slits.

10. The catheter of claim 9, wherein the ramp is substantially conical.

11. The catheter of claim 9, wherein the ramp is substantially shaped as a portion of a sphere.

12. The catheter of claim 9, wherein the ramp is substantially symmetrical with respect to the longitudinal axis of the catheter.

13. The catheter of claim 9, wherein the ramp includes a guiding structure adapted to guide an end of an instrument inserted through the lumen away from the vertex and toward a first one of the slits.

14. The catheter of claim 9, wherein the proximal end of the ramp projects proximally beyond distal ends of all of the slits.

15. The catheter of claim 9, wherein the slits extend substantially in a plane including a longitudinal axis of the catheter.

16. The catheter of claim 9, wherein the valve is substantially conic.

17. The catheter of claim 9, wherein the slits are biased by a resilience of the material of the valve toward a closed position in which the valve is sealed and are moved to an open position permitting fluid flow therethrough only when a fluid pressure applied to the valve exceeds a predetermined threshold value.

\* \* \* \* \*